United States Patent [19]

Hogan

[11] Patent Number: 5,554,896
[45] Date of Patent: Sep. 10, 1996

[54] PORTABLE POWER SUPPLY FOR HANDPIECES

[75] Inventor: Donald J. Hogan, Carlsbad, Calif.

[73] Assignee: Miyad, Del Mar, Calif.

[21] Appl. No.: 331,985

[22] Filed: Oct. 28, 1994

[51] Int. Cl.⁶ .................................................. H02J 7/00
[52] U.S. Cl. ........................... 307/150; 307/118; 604/22; 604/21; 433/82; 433/119; 235/472
[58] Field of Search ................................. 307/150, 116, 307/118; 604/22, 65, 21; 433/29, 119, 80, 82; 320/2; 324/326, 329; 235/472

[56] References Cited

U.S. PATENT DOCUMENTS

| | | | |
|---|---|---|---|
| 2,629,539 | 2/1953 | Drewes, Jr. | 230/58 |
| 3,077,665 | 2/1963 | Saltzman | 32/22 |
| 3,081,542 | 3/1963 | Sherfey | 32/22 |
| 3,553,840 | 1/1971 | Bordelon | 32/22 |
| 4,286,949 | 9/1981 | Holt | 433/116 |
| 4,463,759 | 8/1984 | Garito et al. | 128/303.14 |
| 5,019,767 | 5/1991 | Shirai et al. | 320/2 |
| 5,136,469 | 8/1992 | Carusillo et al. | 361/397 |
| 5,324,197 | 6/1994 | Shain et al. | 433/29 |
| 5,429,601 | 7/1995 | Conley et al. | 604/25 |

Primary Examiner—William M. Shoop, Jr.
Assistant Examiner—Albert W. Paladini
Attorney, Agent, or Firm—Knobbe, Martens, Olson & Bear

[57] ABSTRACT

A portable power supply system utilizes a foot controller and a lightweight, sealed electric motor assembly which attaches to any International Standard E-Coupling handpiece. The foot controller is adaptable for use with either an AC/DC adaptor or a rechargeable battery. A coaxial cable connects the variable voltage supply from the foot controller to the low voltage, DC motor assembly. The motor assembly is sterilizable, lightweight, and quiet, making it ideal for use by dentists, oral or orthopedic surgeons, laboratory technicians, or anyone else desiring an economical, portable power supply for handpieces.

20 Claims, 3 Drawing Sheets

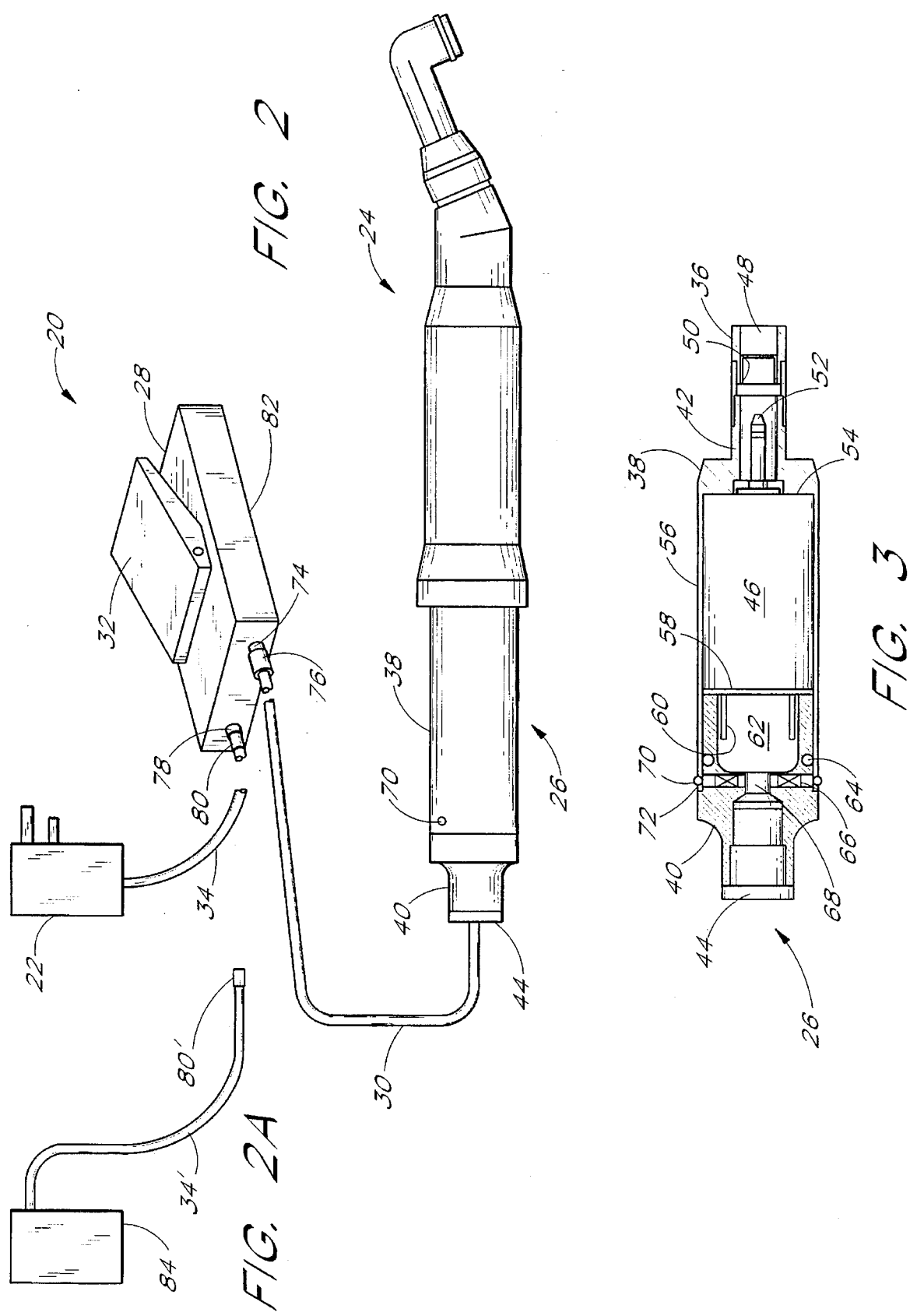

PORTABLE POWER SUPPLY FOR HANDPIECES

BACKGROUND OF THE INVENTION

The present invention pertains to the field of power supply systems for dental, surgical, and industrial handpieces and the like, and, in particular, to a portable, sterilizable, electric power supply which includes an independent power source.

Handpieces or hand tools are used by a variety of professionals, such as dentists, surgeons, technicians, etc. They operate by means of a "power supply" which may utilize electrical or pneumatic energy to drive or power the tool. When handpieces are required to be used in locations outside of normal offices, they may utilize a portable power supply. These outside locations include patient homes, nursing facilities, remote clinics, and other field locations, such as disaster sites or battlefields. Thus, portable power supplies for handpieces are desirable for use in situations where the doctor or technician does not have access to normal office equipment.

While some portable electric power supplies exist, most are pneumatic; although, both electric and pneumatic power supplies are rather large, noisy, and expensive. One example of a portable pneumatic power supply is described in U.S. Pat. No. 4,286,949 issued to Holt, Jr.. Electric power supplies are not typically sterilizable because their components are not sealed, and they are subject to lack of power and power failures because they rely on electrical lines at the site. Although the pneumatic power supplies are sterilizable, they also rely on electrical lines at the site, which may not be available, to power the pneumatic compressor. In addition, pneumatic power supplies require costly maintenance because of the lubricated components which comprise the compressor-motor assembly. Sterilization is highly desirable because of the often infectious environments in which the handpieces may be used. A noise suppression box may be used with these types of portable power supplies, however this only adds to the cumbersome nature and decreases portability.

Thus, a need exists for an improved portable power supply for handpieces that overcomes the problems associated with prior art devices.

SUMMARY OF THE INVENTION

The portable power supply system of the present invention overcomes those problems by including (i) a sealed, sterilizable electric motor assembly which is attachable to a variety of standardized handpieces or handheld tools, and (ii) detachable connection of the motor assembly to a variable voltage foot controller which is adaptable to either an AC/DC adaptor or a rechargeable battery. Thus, the power supply system of the present invention has a motor assembly that is readily autoclavable, is not dependent upon the availability of power at a remote site, is compact and economical, and may be used with any International Standard (ISO) 3954-1982E type handpiece or common laboratory tools.

The variable voltage controller is comprised of a standard foot controller, such as used for sewing machines, with connections for either the AC/DC adaptor or the battery. A conventional coaxial cable is used to communicate the DC voltage output from the foot controller to the electric motor, which is housed in a small, lightweight body with an International Standard male connection at one end. The body is completely sealed, thereby virtually eliminating maintenance requirements and allowing the motor assembly to be autoclaved or sterilized between uses.

The resulting power supply system of the present invention is more compact and quieter than existing systems, and the low voltage requirements of the motor assembly result in added economy. The elimination of the need to clean and replace lubricated parts, which is required in pneumatic systems, further results in ecological benefits, as well as cost savings to the user. The simple, compact structure of the motor assembly results in reduced manufacturing costs, and the use of conventional connections and a commercially available foot controller further adds to a less expensive system.

Further advantages and applications will become apparent to those skilled in the art from the following detailed description and the drawings referenced herein.

BRIEF DESCRIPTION OF THE DRAWINGS

FIG. 2 is a perspective view illustrating an embodiment of the portable power supply system of the present invention, wherein an electrical adaptor is used.

FIG. 2a is a perspective view illustrating an alternate embodiment of the portable power supply system, wherein a rechargeable battery unit is utilized.

FIG. 3 is a partially cross-section view of the motor assembly of the portable power supply system of the present invention as shown in FIG. 2.

DETAILED DESCRIPTION OF THE PREFERRED EMBODIMENT

Figure 1:
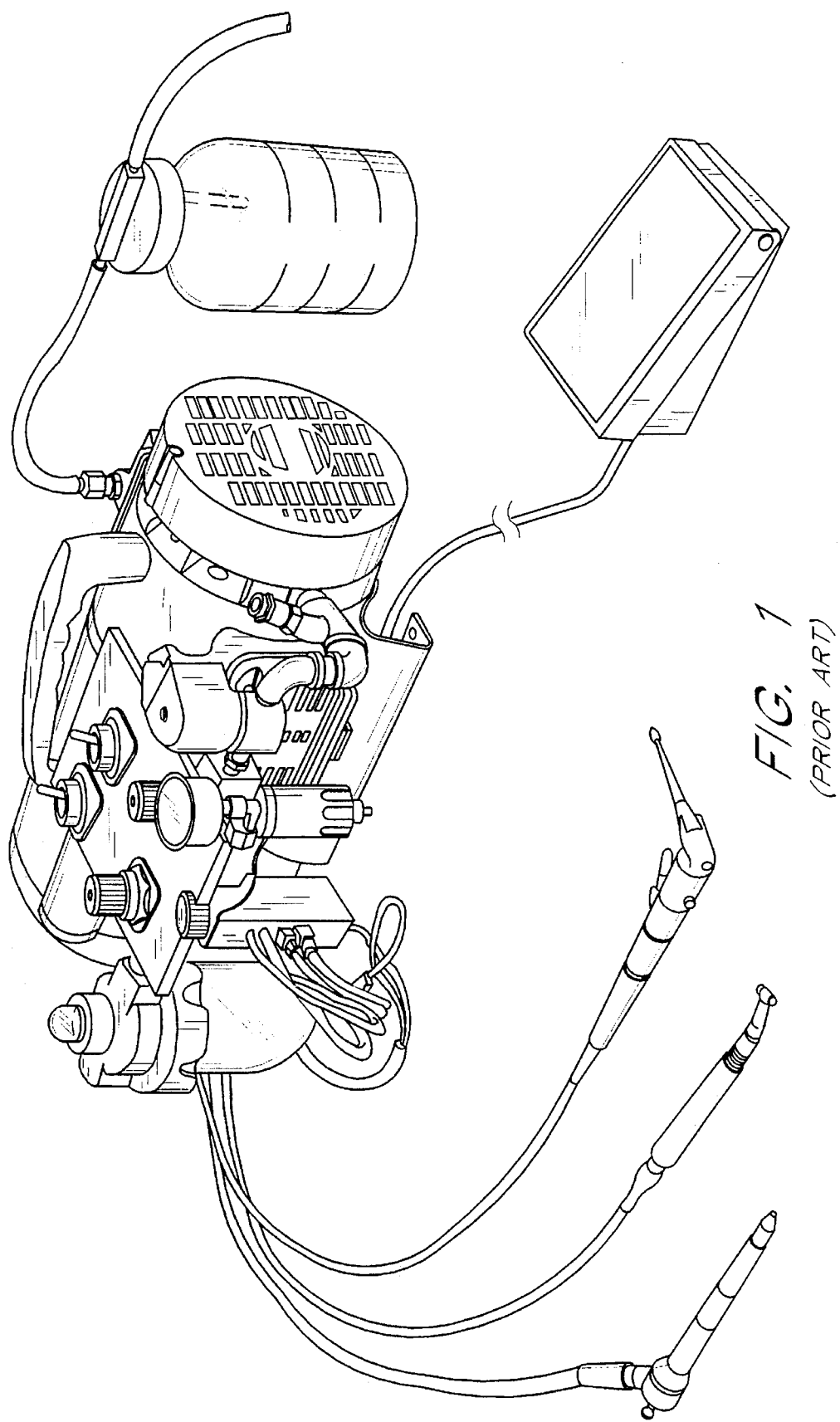
FIG. 1 is a perspective view of a pneumatic power supply system of the prior art.

As illustrated in FIG. 1, the portable power supply systems of the prior art are relatively large and cumbersome, and are typically noisy. The pneumatic power supply system 10 shown in FIG. 1 further requires greater maintenance effort and expense due to its movable, working parts.

In contrast, the portable power supply system of the present invention, illustrated in FIG. 2 and indicated generally by the reference numeral 20, is compact, lightweight, quiet, and substantially maintenance-free. The basic components of the system include an access to an electrical power source and a variable voltage controller. The variable voltage controller controls the current from the higher voltage power source to a low voltage, direct current (DC) motor assembly attached to the proximal end of a handpiece.

In the embodiment illustrated in FIG. 2, the electrical power source is a typical alternating current (AC) outlet (not shown), and the access is provided by an AC/DC adaptor 22, of any conventional type well known to those skilled in the art. Since standard outlet voltage varies in different parts of the world, AC/DC adaptors appropriate to the local electrical supply may be used. Although, as shown in FIG. 2a, the reliance on working electricity in any part of the world can be eliminated by the use of a rechargeable battery unit 84 as the power source for the system 20 of the present invention.

Further, as shown in the prior art system 10 of FIG. 1, there are several types of handpieces available for use with a portable power supply. Accordingly, the handpiece 24 illustrated in FIG. 2 for the portable system 20 of the present invention serves merely as an illustration of the handpieces which may be accommodated.

Referring now in detail to the system 20 of the present invention illustrated in FIG. 2, it can be seen that the handpiece 24 is accommodated at its proximal end to the distal end of the motor assembly 26. The compact motor assembly 26, in turn, is connected at its proximal end to the foot controller 28 via a conventional coaxial cable 30. The foot controller 28 is of a standard type capable of varying the voltage from its power source and delivering a reduced voltage to the motor assembly 26. Pressure by a foot on the lever 32 activates the delivery of current through the controller 28, and increased pressure by the foot results in increased current or voltage. Thus, the doctor or operator has only to use one hand to maneuver the handpiece 24, while his foot operates the motor assembly 26 and the other hand is free to perform other tasks. It should be noted in FIG. 2 that a connecting cable 34 between the AC/DC adaptor 22 and foot controller 28 is of adequate length to allow the foot controller 28 to be located on the ground proximate the patient, away from the outlet, and the coaxial cable 30 is of a length adequate to allow the handpiece 24 to be held by the doctor when standing adjacent the patient.

As shown in FIG. 2, the lever 32 is hinged at its end closest to the connections. The lever 32 is of a rectangular shape covering substantially the entirety of the top of the body 82 of the controller 28. The construction and operation of the foot controller 28 are well-known to those skilled in the art.

The foot controller 28 has two connections in the supply system 20 of the present invention. One connector 74 is male and is inserted into the female connector 76 on the proximal end of the coaxial cable 30 which is attached to the motor assembly 26. The other connector 78 is female and receives the male connector 80 from the cable 34 attached to the AC/DC adaptor 22.

Alternately, as illustrated in FIG. 2a, the battery unit 84 has a connector 80' for mating with the foot controller 28 in lieu of the AC/DC adaptor 22. The use of the battery 84 allows the power supply system to be used in remote locations either not having access to electricity or having undependable electrical supply. The battery unit 84 is preferably of a rechargeable type for economy, although any battery type of adequate voltage having the appropriate connector 80' and cable 34' may be used.

Referring now to FIG. 3, the motor assembly 26 is illustrated (viewed right to left) with its retainer 36, housing 38, and end cap 40 shown in cross-section. The distal end of the assembly 26 comprises a male connector portion 42 of a type known as an International Standard male E-coupling. This connector 42 provides versatility in accommodating any of a variety of handpieces having the corresponding female connector portion (not shown) on its proximal end. The proximal end of the motor assembly 26 comprises a female connector 44 to receive a male connector (not shown) of the coaxial cable 30. When the handpiece 24 and the coaxial cable 30 are removed, the motor assembly 26 may be sterilized without harm to the DC electric motor 46 contained within the housing 38, since the housing 38 is well-sealed, as described below in connection with FIG. 3.

When the handpiece 24 is inserted over the standard ISO male connector 42 of the motor assembly 26, a cylindrical portion (not shown) located within the proximal end of the handpiece 24 is received into a passage 48 of the connector 42. A spring 50 located proximal the retainer 36 provides the tight fit necessary to affix the handpiece 24 onto the motor assembly 26. A driving pin 52 of the electric motor 46 extrudes into the passage 48 and provides the necessary rotary energy to drive the handpiece 24.

As shown in FIG. 3, the pin 52 is centrally located on a distal face 54 of the electric motor 46. The housing 38 encasing the pin 52 and motor 46 has a main body 56 with an inner diameter substantially the same as the diameter of the electric motor 46, thus ensuring a tight, sealing fit. A high temperature, preferably silicone, sealant is used on the distal face 54 of the motor 46 to provide additional sealing in the housing 38. A spring washer 58 is similarly sized to fit within the housing 38 and engages the proximal end of the motor 46. The spring washer 58 biases the motor 46 distally so that its distal face 54 is further provided with a secure seal. Connectors 60 extrude from the proximal end of the motor 46 through apertures (not shown) in the washer 58, and are received into a cavity 62 formed at the distal end of the end cap 40.

The distal end of the end cap 40 also has an outer diameter substantially the same as the inner diameter of the housing's main body 56, in which it is engaged. The exterior of the distal half of the end cap 40 is fluted, wherein the distal end has a reduced outer diameter adequate to receive the widest, distal portion of the connector 44. The connector 44 is hermetically sealed in the end cap 40. An O-ring 64 is located proximate the proximal end of the housing 38 to further provide sealing of the motor assembly 26. Thus, the sealant applied to the distal face 54, the spring washer 58, and the O-ring 64 components, along with other components and tolerances, hermetically seal the motor 46 within the housing 38.

Engagement of the end cap 40 onto the proximal end of the housing 38 is accomplished via springs 66 surrounding a passage 68 communicating the Cable connector 44 to the cavity 62. The springs 66 provide outward pressure on pins 70 which extend through holes 72 located on the periphery of the proximal end of the housing 38. Thus, the end cap 40 is removable by manually depressing the pins 70, if necessary for service or maintenance.

Wires (not shown) for the electrical connection between the connectors 60 and the connector 44 extend from the cavity 62 through the passage 68. Thus, the connector 44 comprises a "jack-type" electrical connector which receives the probe of the male connector on the distal end of the cable 30. The connector 44 has a distal portion of a reduced diameter comprising one electrode and a more proximal portion of a larger diameter comprising the other electrode of the opposite charge. These charges are provided by wires soldered to the connectors 60. Thus, the electrical connection between the cable 30 and connectors 60 is accomplished.

Figure 4:
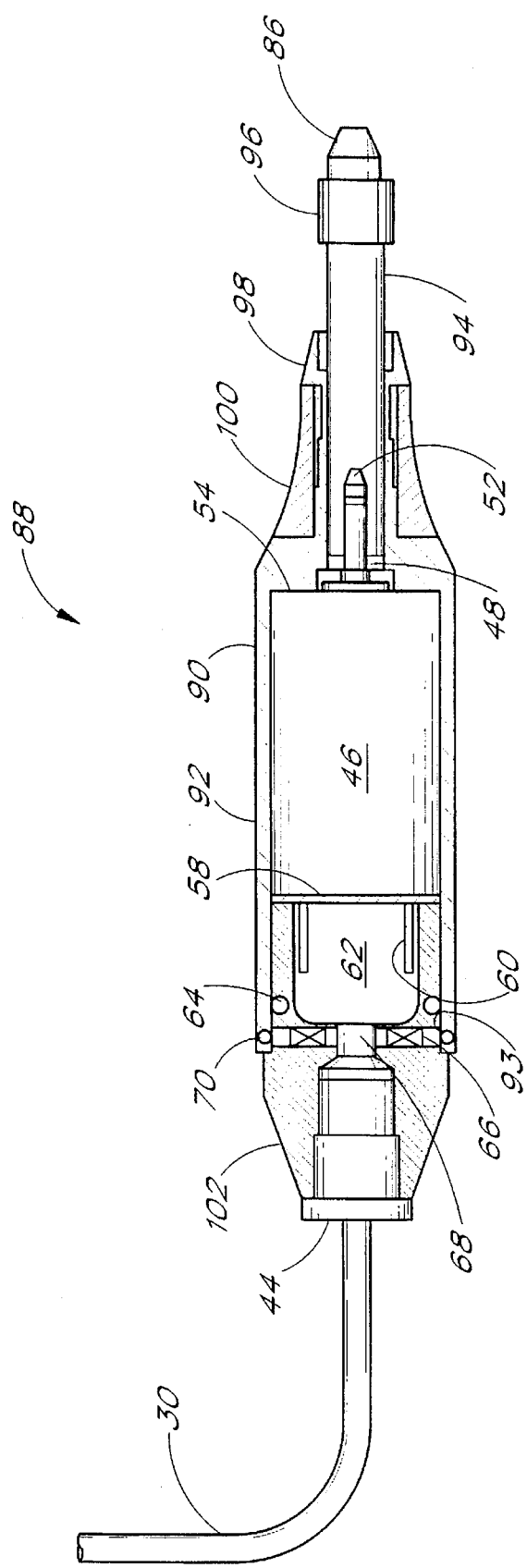
FIG. 4 is a partially cross-section view of an alternate embodiment of the motor assembly of the portable power supply system of the present invention.

A motor assembly of the system 20 of the present invention is not only operable as an extension to a handpiece, but may also be used as a handle and power supply for small tools such as used in laboratories. That is, a chuck and collet configuration may be used in place of the male E-coupling to attach various tools or bits rather than ISO E-type handpieces, as illustrated in FIG. 4. Laboratory technicians and the like can thus use an alternate embodiment of the motor assembly to attach a tool 86 directly onto the distal end of the motor assembly 88, with the housing 90 of the assembly 88 comprising the handle necessary to grip and maneuver the tool 86.

As illustrated in FIG. 4, the DC motor 46 is contained within substantially the same casing as the previous motor assembly 26 of FIG. 3. Here, like numbers refer to like parts.

The housing 90 includes a main body 92 having a slightly larger outer diameter than the housing 38. This larger diameter allows the pins 70 to be contained in recesses 93 formed on the inner circumference of the body 92. Thus, the pins 70 do not extrude to the exterior of the housing 90.

In the motor assembly of FIG. 4, the distal end is adapted to include a shaft 94 and nut 96 for attachment of the tool 86. The nut 96 is located on the distal end of the shaft 94, and the tool 86 is simply inserted and the nut releasably tightened. Thus, the exchange of tools is simple and quickly accomplished.

The shaft 94 has an outer diameter substantially the same as the passage 48 and extends to proximate the base of the driving pin 52. A nut 98 replaces the retainer 36 of the other motor assembly 26 and affixes the shaft 94 to the distal end of the housing 90. A smoothly contoured spacer 100 surrounds what was the male connector 42 of the other assembly 26, and together with a tapered outer surface of the end cap 102, provides a more uniform and better feeling exterior for handling by the technician.

Accordingly, the portable power supply 20 of the present invention provides a compact and multi-functional power source for doctors and others requiring same. The ISO compatible male connector 42 of the motor assembly 26 in one embodiment can accommodate a variety of handpieces, as likewise the shaft 94 and nut 96 of the motor assembly 88 in another embodiment can accommodate a variety of hand-held tools. An AC/DC adaptor 22 appropriate for the local electricity may be used, or a battery unit 84 may be substituted in remote or more hostile locations. Finally, the sealed casings of motor assemblies 26 and 88 significantly reduces the incumbent maintenance of the power supply 20, and further allows the motor assembly 26 or 88 to be sterilized as required along with the handpieces or tools.

Thus, the electric power supply system 20 of the present invention affords versatility, portability, and reliability heretofore unavailable. Other changes and modifications may be made from the embodiments presented herein by those skilled in the art without departure from the spirit and scope of the invention, as defined by the appended claims.

What is claimed is:

1. A portable power supply system for handpieces comprising:
   a variable voltage foot controller having a disconnectable electrical power source comprised of a rechargeable battery unit;
   a sealed and sterilizable electric motor assembly including a distal end having a male coupling for type ISO-3954-1982E handpieces and a proximal end having a connector; and
   a coaxial cable connected at one end to the variable voltage foot controller and at the other end to said connector on said proximal end of the sealed electric motor assembly.

2. The power supply system of claim 1, wherein said disconnectable electrical power source is an AC/DC adaptor for plugging into an electrical outlet.

3. A portable power supply system for hand-held laboratory tools comprising:
   a variable voltage foot controller having a disconnectable electrical power source comprised of a rechargeable battery unit;
   a housing;
   a sealed and sterilizable electric motor assembly disposed within the housing and including a distal end for receiving a laboratory tool and a proximal end having a connector, said connector hermetically sealed in said proximal end, the sealed electric motor assembly further including an electric motor distal to said connector and sealed at its distal end;
   a spring washer biasing said motor against the housing;
   an O-ring positioned between said connector and said motor; and
   a coaxial cable connected at one end to the variable voltage foot controller and at the other end to said connector on said proximal end of the sealed electric motor assembly.

4. The power supply system of claim 3, wherein said disconnectable electrical power source is an AC/DC adaptor for plugging into an electrical outlet.

5. A portable power supply system for handpieces comprising:
   a foot controller having a connector for detachably receiving an electrical power source;
   a cable including a first end and a second end, said first end having a first connector for attachment to the foot controller, said second end having a second connector; and
   a sterilizable motor assembly having a distal end for receiving a handpiece and a proximal end for attachment to said second connector on said second end of the cable.

6. The power supply system of claim 5, wherein said electrical power source is an AC/DC adaptor for plugging into an electrical outlet.

7. The power supply system of claim 5, wherein said electrical power source is a rechargeable battery unit.

8. The power supply system of claim 5, the motor assembly further having a male coupling on said distal end for receiving a type ISO-3954-1982E handpiece.

9. The power supply system of claim 5, wherein the foot controller is a variable voltage type.

10. A portable power supply system for hand-held tools comprising:
    a foot controller having a connector for detachably receiving an electrical power source;
    a cable including a first end and a second end, said first end having a first connector for attachment to the foot controller, said second end having a second connector; and
    a sterilizable motor assembly having a distal end for receiving a laboratory tool and a proximal end for attachment to said second connector on said second end of the cable.

11. The power supply system of claim 10, wherein the foot controller is a variable voltage type.

12. The power supply system of claim 10, wherein said electrical power source is an AC/DC adaptor for plugging into an electrical outlet.

13. The power supply system of claim 10, wherein said electrical power source is a rechargeable battery unit.

14. The power supply system of claim 10, wherein said distal end of the motor assembly has a chuck and collet for receiving said tool.

15. A portable power supply system for handpieces comprising:
    a variable power controller;
    a power transmitter coupled to the variable power controller; and
    a sterilizable motor assembly coupled to said power transmitter and receiving said handpiece.

16. A portable power supply system for handpieces or hand-held laboratory tools comprising:
- a variable voltage foot controller having a first connector for attachment to a battery unit or an AC/DC electrical adaptor;
- a cable detachably connected on a first end to a second connector on the variable voltage foot controller; and
- a sealed and sterilizable motor assembly having a distal end for receiving a handpiece or a hand-held laboratory tool and a proximal end for detachable connection to a second end of the cable.

17. A portable power supply system for hand-held tools comprising:
- a foot controller having a connector for detachably receiving an electrical power source;
- a cable including a first end and a second end, said first end having a first connector for attachment to the foot controller, said second end having a second connector; and
- a motor assembly having a distal end having a chuck and collet for receiving a laboratory tool and a proximal end for attachment to said second connector on said second end of the cable.

18. The power supply system of claim 17, wherein said electrical power source is an AC/DC adaptor for plugging into an electrical outlet.

19. The power supply system of claim 17, wherein said electrical power source is a rechargeable battery unit.

20. The power supply system of claim 17, wherein the motor assembly is sealed and sterilizable.

* * * * *